United States Patent [19]
Nolte et al.

[11] Patent Number: 5,307,694
[45] Date of Patent: May 3, 1994

[54] SAMPLE HOLDER FOR HYDROUS PYROLYSIS OPERATIONS

[75] Inventors: David G. Nolte; Helen K. Haskin, both of Houston; Edwin L. Colling, Jr., Sugar Land, all of Tex.

[73] Assignee: Texaco Inc., White Plains, N.Y.

[21] Appl. No.: 884,578

[22] Filed: May 18, 1992

Related U.S. Application Data

[62] Division of Ser. No. 740,744, Aug. 6, 1991, U.S. Pat. No. 5,180,556, which is a division of Ser. No. 455,112, Dec. 22, 1989, U.S. Pat. No. 5,082,787.

[51] Int. Cl.$^5$ .............................................. G01N 1/00
[52] U.S. Cl. ................. 73/863.23; 73/864.91
[58] Field of Search ............. 73/863, 863.23, 38, 73/864.91; 422/78, 102; 220/371; 215/261; 210/510.1, 335, 446, 232, 459, 449, 339

[56] References Cited

U.S. PATENT DOCUMENTS

| | | | |
|---|---|---|---|
| 2,618,151 | 11/1952 | Leas | 73/38 |
| 2,676,485 | 4/1954 | Morgan | 73/38 |
| 3,972,225 | 8/1976 | Fort et al. | 73/863.23 |
| 4,301,114 | 11/1981 | Rounbehler et al. | 422/78 |
| 4,643,019 | 2/1987 | Jones . | |

*Primary Examiner*—Hezron E. Williams
*Assistant Examiner*—Nashmiya Ashraf
*Attorney, Agent, or Firm*—James L. Bailey; Kenneth R. Priem; Russell J. Egan

[57] ABSTRACT

A sample holder for use in hydrous pyrolysis operations has a cylindrical member defining an axial throughbore with like discs of fluid permeable material at each end. One disc is fixed in the cylindrical member and the other removably attached for insertion of a sample into the holder. The holder has at least one end shaped so as to prevent sealing from occurring when the holder is placed in a test chamber.

2 Claims, 3 Drawing Sheets

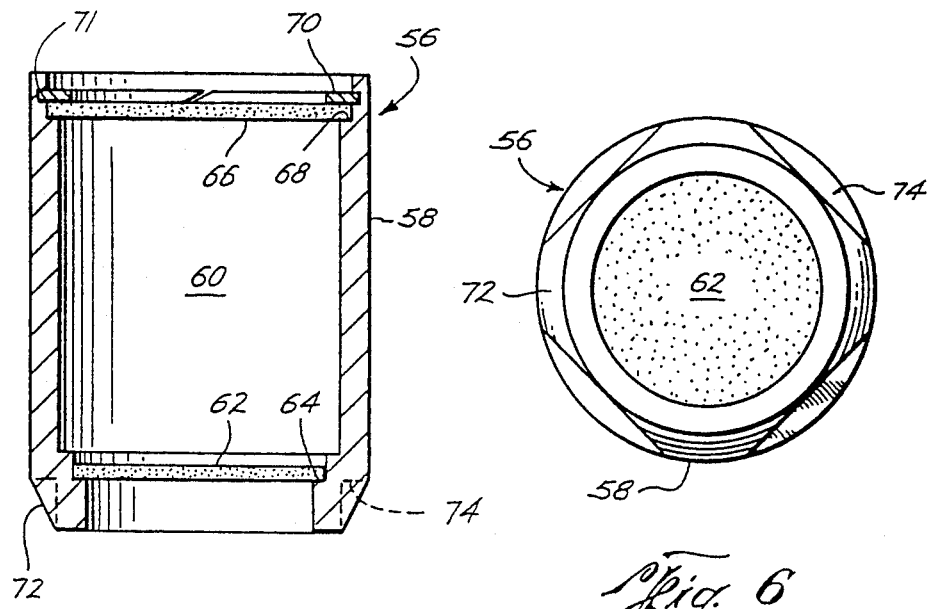
Fig. 5
Fig. 6
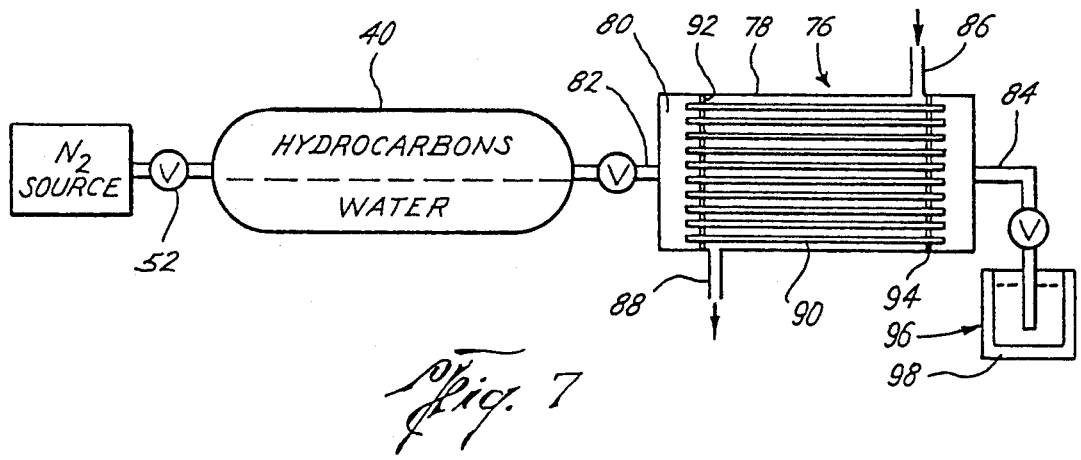
Fig. 7

SAMPLE HOLDER FOR HYDROUS PYROLYSIS OPERATIONS

This is a division of copending U.S. patent application Ser. No. 07/740,744 filed Aug. 6, 1991, now U.S. Pat. No. 5,180,556 which in turn is a divisional application of Ser. No. 07/455,112, filed Dec. 22, 1989, now U.S. Pat. No. 5,082,787.

BACKGROUND OF THE INVENTION

1. The Field Of The Invention

The present invention relates to a method and apparatus for determining, in the laboratory, the rate and type of hydrocarbon generation by a hydrocarbon source.

2. The Prior Art

The total amount of hydrocarbons that can be generated and the relative amounts of oil and gas in these hydrocarbons depend upon the composition of the parent kerogen in the petroleum source bed. Kerogen is the insoluble organic matter in sedimentary rock which is capable of generating hydrocarbons upon being heated.

Two broad types of dispersed kerogen can be recognized in sediment. Type I, commonly referred to as sapropelic kerogen, contains amorphous algal remains, enriched in long chain aliphatic side branches and has an original high hydrogen content and relatively low oxygen/carbon ratio. Upon thermal maturation, sapropelic kerogen yields mainly oil. Type III, referred to as humic kerogen, consists of land-plant derived lignitic and cellulosic constituents and is poor in aliphatic side chains. It has a low hydrogen content and a relatively high oxygen/carbon ratio. Upon thermal maturation, humic kerogen yields mainly gas. A mixture of humic and sapropelic kerogen, commonly referred to as Type II, will yield both oil and gas upon thermal maturation.

Heating kerogen causes thermal degrading in a predictable manner by releasing hydrocarbons and condensing the solid organic structure. The maturation of kerogen can be accelerated by conducting the reaction in an oxygen free atmosphere at temperatures higher than those commonly encountered in natural systems. Heating kerogen isothermally at elevated temperatures and pressures in the presence of water is a process referred to variously as hydrous pyrolysis, simulated maturation or sealed vessel pyrolysis.

The explorationist must correctly model the rate of oil and gas generation to prepare an estimate of the potential hydrocarbon volume in a frontier basin. Most previously published studies of the kinetics of oil and gas generation from hydrocarbon source material have been done using Rock-Eval pyrolysis. This is a popular method because the instruments are readily available. The procedure involves heating a sample, in a flowing helium stream, from room temperature to 550° C. in 30 minutes. This is relatively fast but the results are sensitive to sample texture and temperature measurement and control. Data analysis is complicated by the non-isothermal nature of the experiment.

Better quality kinetic data is obtainable from isothermal experiments in a closed system. Hydrous pyrolysis involves isothermal heating of the source material with water in a closed system, but product recovery problems have limited its application to qualitative studies of oil and bitumen generation.

The better examples of the prior art in this area are "A Laboratory Study Of Petroleum Generation By Hydrous pyrolysis" by Winters et al. Advances in Organic Geochemistry, 1981 M. Bjoroy ed. New York Wiley 1983, pp. 524-532; "Comparison of Methods for Measuring Kerogen Pyrolysis Rates and Fitting Kinetic Parameters" by Burnham et al. UCRL-95660 193rd Meeting of the American Chemical Society, Denver, Colo. (Apr. 5, 1987); "Comparison between natural and artificial maturation series of humic coals from the Mahakam delta, Indonesia" Monthioux et al. Org. Geochem. Vol. 8, No. 4, pp. 275-292, 1985; and "The microscale simulation of maturation: outline of a new technique and its potential applications" Horsfield et al. Geologische Rundschau 78/1 pp. 361-374 Struttgart 1989.

The Winters et al. publication is of particular interest in that it teaches the use of a closed reactor for heating kerogen, oil shale or hydrocarbon source materials, controlling and recording temperature at a specific value, means to purge the reactor with inert gas, hot transfer to a recovery vessel of the volatile products in a batch method, recovering bitumen from the reactor chamber through the use of solvents, and sampling the gases recovered and venting the rest. While this is somewhat similar to the present invention, it does not utilize a sample holder to confine the solids, use oxygen purged water, recover soluble bitumen from the sample holder by washing with solvents, or recover the low boiling oils from the water by a second cryogenic transfer with dryer means for removing the water. Thus the present invention enables a more complete analysis of the hydrocarbon sample.

The Monthioux et al. and Horsfield et al. articles describe methods for artificially maturing kerogen in closed systems in the absence of water. These methods have been used only for qualitative characterization of products resulting from kerogen maturation.

SUMMARY OF THE INVENTION

The present invention concerns a method and apparatus by which the kinetics of kerogen maturation can be studied under carefully controlled laboratory conditions and with a high degree of accuracy. The present invention uses hydrous pyrolysis to effect a material balance by quantitative recovery of the reaction products in six distillation cuts. The reaction can be carried out with whole rock or, to avoid the effects of the mineral matrix, with the isolated kerogen. The subject method and apparatus solves the problem of pyrolysis product recovery.

BRIEF DESCRIPTION OF THE DRAWINGS

The present invention will be described by way of example with reference to the accompanying drawings in which:

FIG. 5 is a vertical section through the sample capsule used in the subject invention;

FIG. 6 is a bottom plan view of the capsule of FIG. 5; and

FIG. 7 is a diagrammatic side elevation, partly in section, of a dryer.

DETAILED DESCRIPTION OF THE PREFERRED EMBODIMENT

Figure 1:
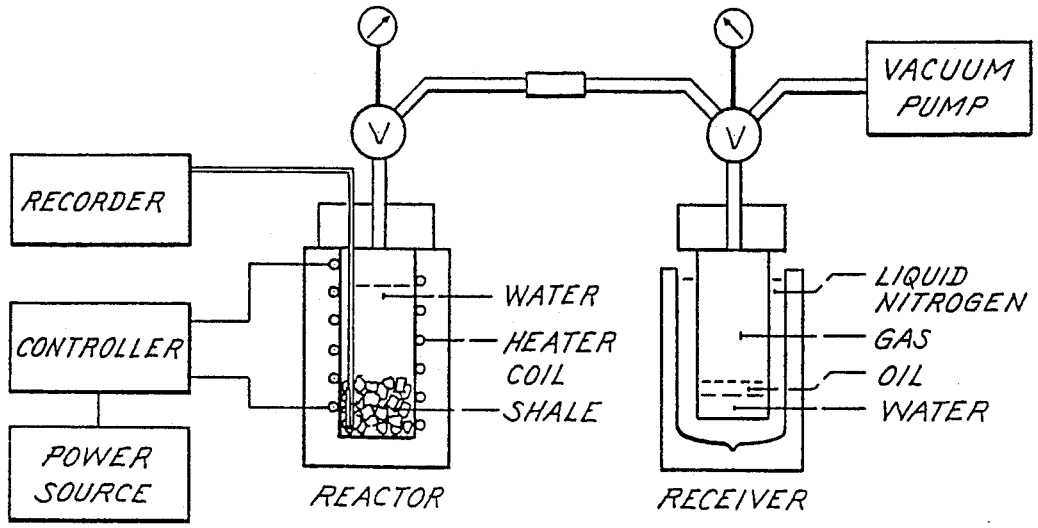
FIG. 1 is a schematic representation of the prior art method.

An example of the prior art is illustrated in FIG. 1. This is the apparatus suggested by Winters et al. in the above cited article. The sample is placed in the reactor shown on the left of the drawing. The vessel contents are heated to the desired temperature for a prescribed time. The identical preconnected pressure vessel, shown on the right, which has been evacuated and cooled, is opened slowly to the hot reactor. The rate of transfer is controlled by valve means to allow all of the water and other condensables to liquify, thereby maintaining maximum pressure differential between the two vessels. When the pressure differential approaches zero, essentially all of the water, gas and volatile products will have transferred to the receiver. This method allows recovery of volatile components but does not transfer heavy resins and asphaltenes.

Figure 4:
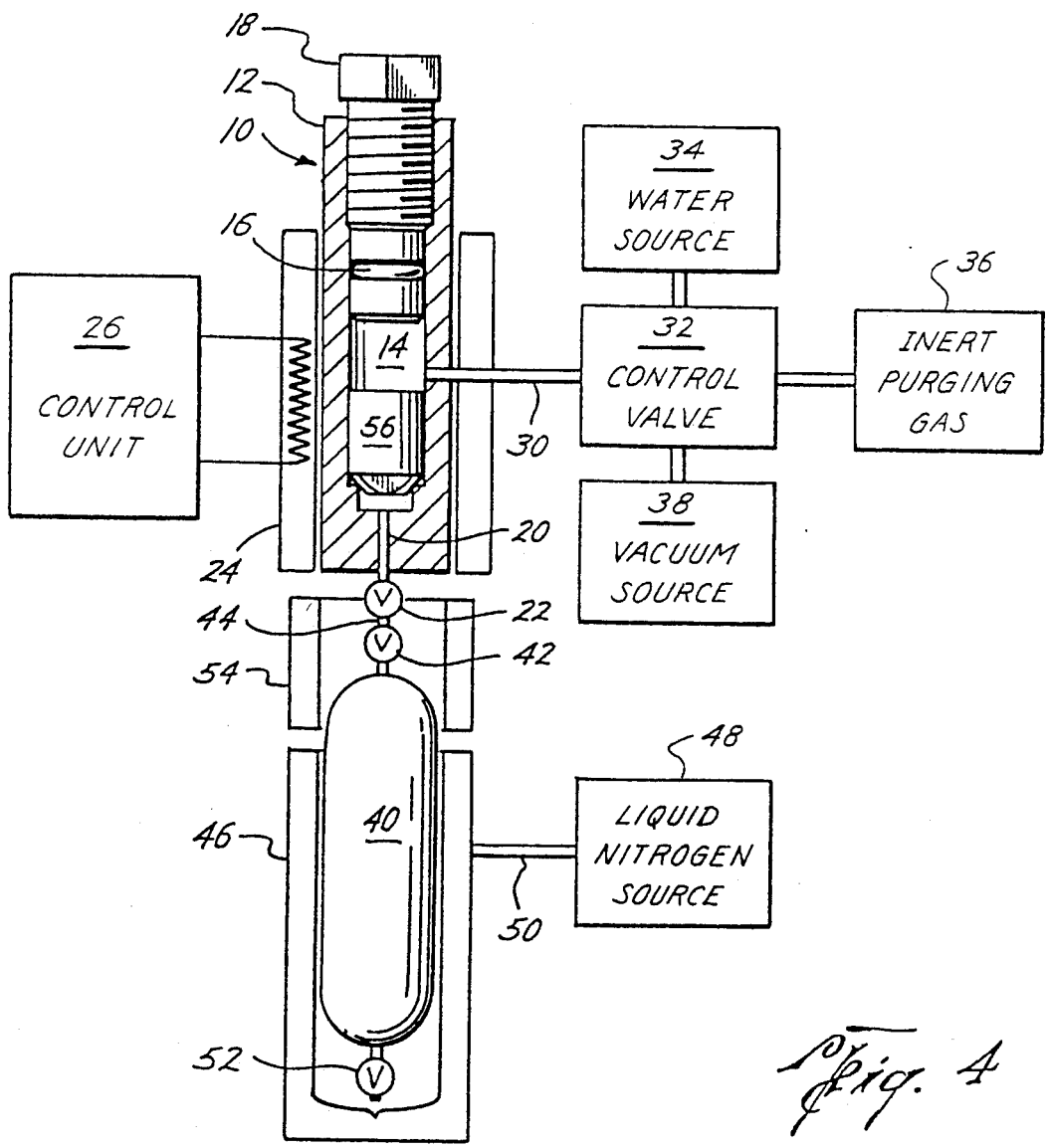
FIG. 4 is a schematic of the apparatus for practicing the subject method.

The apparatus for practicing the subject invention is schematically shown in FIG. 4. The apparatus 10 includes a reactor vessel 12 defining a central chamber 14 of approximately 500 ml volume closed at one end by seal 16 and threaded cap 18 forming a self sealing closure which provides a tighter seal as the internal reactor pressure increases. A drain conduit 20 leads to the lower end of chamber 14 and is closed by a valve 22. This drain distinguishes the present reactor from standard reactors, such as those sold by Autoclave Engineers Inc. Standard features, such as rupture disc assemblies to safely vent the contents of the reactor should pressures be exceeded, have not been shown. The reactor vessel 12 is enclosed in a furnace 24 which is controlled by control unit 26 including heater means, temperature sensing means, recording and timing means, all of which are well-known and therefore have not been illustrated. A fluid system 28 is connected to chamber 14 by conduit 30. The fluid system includes control valve means 32, a source of water 34, a source of inert purging gas 36, and a vacuum source 38. A transfer vessel 40 is connected to drain valve 22 through valve 42 and conduit 44. The transfer vessel is a 500 ml 5000 psi working pressure Monel cylinder and is enclosed in a dewar flask 46. The level of liquid nitrogen in dewar flask 46 is controlled from a source 48 of liquid nitrogen through conduit 50. A drain valve 52 is connected to the lower end of the transfer vessel 40. A heating jacket 54, capable of heating to 350° C., is fastened around the valves 22,42 and conduit 44 between the reaction and transfer vessels 12,40. This prevents the hydrous pyrolysis products from freezing in the valves and lines during cryogenic transfer.

A sample material holder 56 (see FIGS. 5 and 6), proportioned to be loosely received in chamber 14, has a generally cylindrical body 58 defining a central through bore 60. A first disc 62 is force fitted into the lower end of bore 60 against lower shoulder 64 and a second like disc 66 is fitted against upper shoulder 68 and secured in place by split ring 70 received in annular groove 71. The discs are preferably fritted stainless steel 1/16" thick having 0.5 micron pores which allow water to enter the holder and lower molecular weight hydrocarbons, such as gases and oils, to leave. The exterior of the holder 56 is generally cylindrical with a truncated conical lower end 72 which also has a series of hyperbolic surfaces 74 (see FIG. 6) which both prevents a seal from being formed between the holder and the chamber 14 and allows drainage around the holder.

The method of the present invention is practiced by first placing a sample of hydrocarbon source material, such as kerogen or oil shale, in the sample holder shown in FIGS. 4 and 5. Typical sample weights range from 5 to 50 grams and can be in any physical form, such as a large single piece or many smaller pieces. The sample holder 56 is placed into the reactor cavity 14 and the reactor sealed. The recovery cylinder 40, which is suspended in a dewar 46, is attached to the transfer valve 22 through valve 42 and conduit 44 below the reactor 12.

After loading the sample, the reactor and transfer vessels are repeatedly charged with inert purge gas, such as helium, from source 36 and then evacuated by vacuum manifold 38 to completely purge the reactor and transfer vessels of oxygen. The purging of the system is carried out by the chamber control 32. After the last evacuation, the transfer valve 22 is closed (and remains closed until the hydrous pyrolysis is completed). Then two hundred grams of pure water are introduced into the evacuated reactor from the water source 34. This water should at least be distilled or deionized, oxygen-free water and preferably is oxygen-free HPLC grade water. In the preferred embodiment pure water is purged with helium from source 36 under control 32. The reactor 12 is again evacuated and the charge line 30 closed. The furnace 24 is then activated to bring the reactor 12 to the desired temperature, typically 225° to 360° C.

Figure 2:
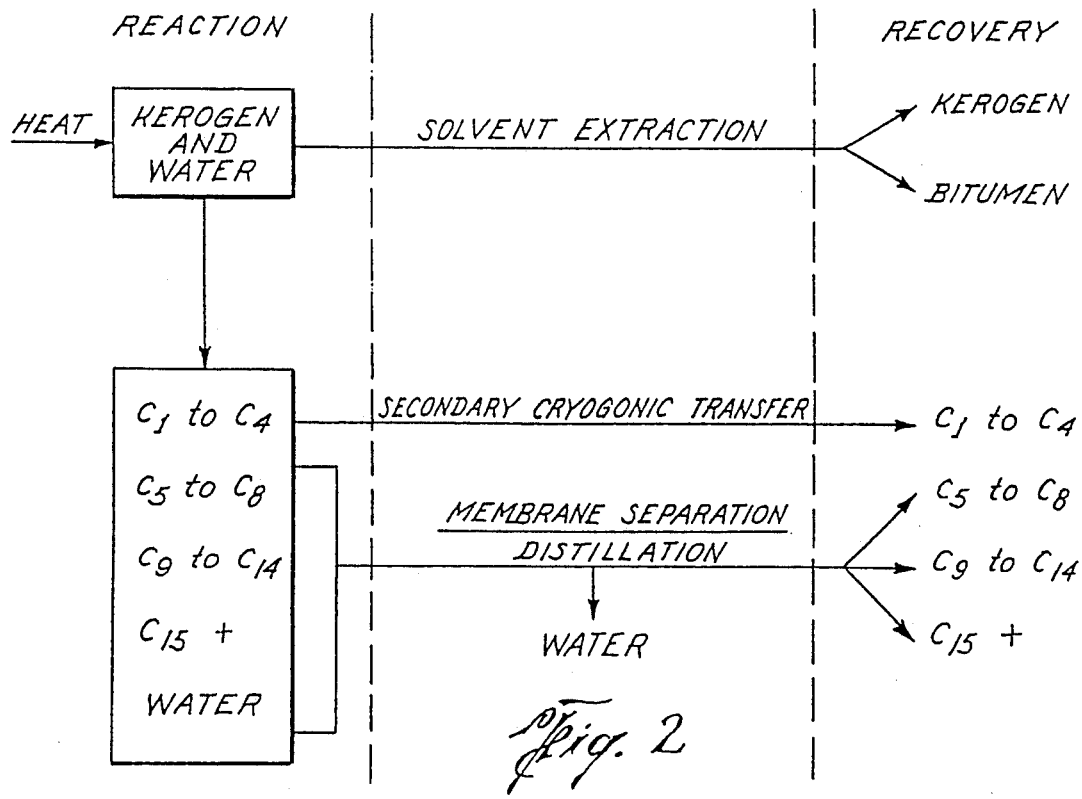
FIG. 2 is a schematic representation of the present method.
Figure 3:
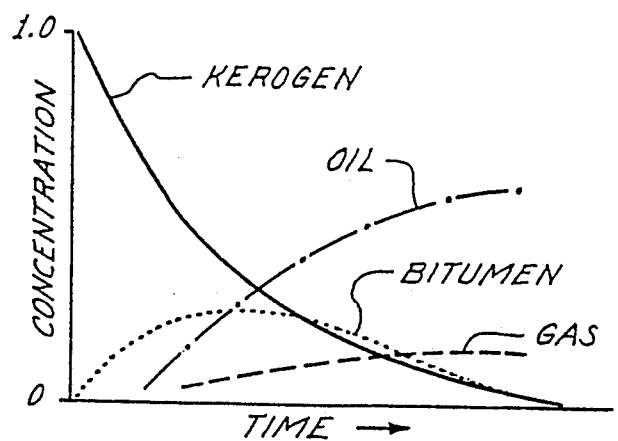
FIG. 3 is a schematic of the kinetics of kerogen maturation.

The major difference between the present invention and general industry practice is the quantitative recovery of all products created by hydrous pyrolysis. The prior art recovered quantitatively only the bitumens and heavy oils and unreacted kerogen or oil shale. The present invention quantitatively recovers all of the unreacted kerogen or oil shale, the bitumen, both light and heavy oils, and the gases produced during hydrous pyrolysis. This is not easy because the presence of 200 grams of water in the reactor during the experiment makes separation and recovery of light hydrocarbons from the water rather difficult. Simple distillation cannot be used because the light hydrocarbons boil at or near the boiling point of water. However, the water is considered necessary to ensure the creation of products similar to those found in nature. The products are recovered quantitatively by combination of cryogenic transfers, solvent extractions and membrane separation techniques. These are shown graphically in FIG. 2.

When the cooking of the sample is completed, the water, oil and gases are transferred cryogenically into a transfer vessel 40 which is bathed in liquid nitrogen and located directly below the still hot reactor 12. The kerogen and bitumen from the sample are left behind in the reactor to be recovered after the reactor cools down. The liquids and gases are drained from the reactor chamber 14 through valves 22 and 42 and conduit 44 into the transfer vessel 40. This is the first cryogenic transfer.

Once the reactor 12 has cooled down, which takes approximately 24 hours, the sample holder 56 containing unreacted kerogen and newly formed bitumen is removed. Soluble bitumen is extracted from the kerogen by conventional processing. Solvent rinsings from the reactor chamber 14 are combined into the solvent extracted bitumen and the weight of the bitumen determined after all solvent is evaporated away.

While the reactor 12 cooled, the transfer cylinder 40 warmed to room temperature in preparation for the second cryogenic transfer. The transfer cylinder 40 is cooled to 0° C. and the gases cryogenically transferred to a smaller vessel (not shown) cooled by liquid nitrogen. The weight of the gas collected is calculated using the ideal gas law, given the volume of the smaller vessel, the pressure of the gas within at some temperature and the molecular weight of the gas sample.

Oil and water are separated using a dryer 76, see FIG. 7, preferably one similar to the Model PD-750-2455 sold by Perma Pure Products, Inc. The dryer 76 has an outer casing 78 defining a central cavity 80 having inlet and outlet ports 82, 84 and purge inlet and outlet ports 86, 88. A bundle of closely spaced, parallel tubes 90 are mounted in cavity 80 between spaced headers 92, 94. The tubes 90 forming the bundle are extruded desiccants. The dryer 76 utilizes hygroscopic ion exchange membranes in a continuous drying process to remove water vapor from the gases passing through the tubes. As the water-oil mixture in the transfer vessel 40 is boiled off, the vapors are passed through the dryer 76. Gasoline range hydrocarbons pass down the dryer and are collected in a container 96 chilled in an isopropanol/dry ice mixture 98 which makes a syrupy bath.

When all of the water-hydrocarbon mixture has boiled off, the transfer cylinder 40 and dryer 76 are cleaned thoroughly with solvent to recovery the heavy portion of the oil. The weight of oil produced is equal to the sum of the weights of the hydrocarbon transfer at the dryer outlet and the solvent-free weights of the oil cleaned from the dryer and transfer cylinder.

Better than 90% recovery of hydrous pyrolysis products can be achieved by the subject method. The evolution of hydrocarbons from kerogen is observed by conducting hydrous pyrolysis experiments at each of several single temperatures for several different times. Hydrocarbon generation occurs very slowly in nature so laboratory hydrous pyrolysis experiments must be carried out at elevated temperatures to provoke measurable maturation in a laboratory study. Typical laboratory temperatures range from 225° to 360° C. Laboratory cooking times range from days to months.

Rates of hydrocarbon evolution measured at high temperatures can be extrapolated to their values at lower temperatures found in nature, if the temperature dependence of the reaction rate constant has been determined. This is done by conducting the hydrous pyrolysis experiments described above at two or more temperatures. The Arrhenius relation is then used to determine the temperature dependence of the chemical reaction rate constants. The rate equations describing the generation of hydrocarbons from source material are developed by measuring the composition of the reaction mixture (weights of bitumen, oil, gas and unreacted kerogen) at various times. Then the data is compared to various types of rate equations to find the one giving the best agreement.

Given a set of rate equations and the proper temperature dependence of their constants, one can estimate the rate of oil and gas generation in nature.

The present invention has been described by way of example and is subject to modification and variation by those skilled in the art. The foregoing description is not intended to limit the scope of the invention which is defined by the appended claims.

What is claimed is:

1. A sample holder to be received in a test chamber of a device for performing hydrous pyrolysis in order to determine the kinetic properties of hydrocarbon generation from a sample of hydrocarbon source material, said holder comprising:

a cylindrical member sample receiving means for holding the hydrocarbon sample and defining an axial sample receiving bore having oppositely directed first and second open ends, a first shoulder adjacent said first end, a second shoulder adjacent said second end, and an annular groove between said second shoulder and said second end, said sample receiving means further adapted to be received in a test chamber of a device for performing hydrous pyrolysis;

a first disc of fluid permeable material force-fitted into said first end of said member against said first shoulder;

a second like disc of fluid permeable material received in said second end of said member against said second shoulder;

said first and second discs formed from fritted stainless steel having pores approximately 0.5 microns in size;

split ring means received in said annular groove to secure said second disc in place against said second shoulder; whereby water can enter the holder as the hydrous pyrolysis operation drives lower molecular weight hydrocarbons out of the sample and the sample holder.

2. A sample holder according to claim 1, wherein at least one end of said receiving means defines a truncated cone with at least one hyperbolic surface thereon whereby said holder can be received in said test chamber without forming a sealing engagement therewith.

* * * * *

UNITED STATES PATENT AND TRADEMARK OFFICE
CERTIFICATE OF CORRECTION

PATENT NO. : 5,307,694
DATED : May 3, 1994
INVENTOR(S) : David Gerard Nolte, Helen Kay Haskin and Edwin Lee Colling, Jr.

It is certified that error appears in the above-indentified patent and that said Letters Patent is hereby corrected as shown below:

Column 6, claim 1, line 21, delete "member".

Signed and Sealed this

Twenty-ninth Day of November, 1994

Attest:

BRUCE LEHMAN

Attesting Officer       Commissioner of Patents and Trademarks